United States Patent [19]

Corner

[11] Patent Number: 4,620,849

[45] Date of Patent: Nov. 4, 1986

[54] METHODS FOR TOPICALLY APPLYING COMPOSITIONS TO SMALL ANIMALS

[76] Inventor: Margit Corner, 7758 Orleans St., Miramar, Fla. 33023

[21] Appl. No.: 674,061

[22] Filed: Nov. 21, 1984

[51] Int. Cl.[4] ............................................. A61M 35/00

[52] U.S. Cl. ..................................... 604/290; 604/293

[58] Field of Search ................ 604/290, 292, 289, 293

[56] References Cited

U.S. PATENT DOCUMENTS

| | | | |
|---|---|---|---|
| 1,562,318 | 11/1925 | Erlandson . | |
| 3,108,568 | 10/1963 | Whitney et al. . | |
| 3,150,641 | 9/1964 | Kesh . | |
| 3,384,083 | 5/1968 | Cozza et al. | 604/292 |
| 3,473,699 | 10/1969 | Pike | 604/292 |
| 4,026,290 | 5/1977 | Brooker et al. | 604/290 |
| 4,050,417 | 9/1977 | Ellis . | |
| 4,169,428 | 10/1979 | Waugh . | |

*Primary Examiner*—John D. Yasko

*Attorney, Agent, or Firm*—Hughes & Cassidy

[57] ABSTRACT

The disclosure relates to a method and apparatus for applying pharmaceutical and other topical compositions to small animals such as cats and dogs.

2 Claims, 4 Drawing Figures

METHODS FOR TOPICALLY APPLYING COMPOSITIONS TO SMALL ANIMALS

The present invention relates to novel, improved methods for applying pharmaceutical and other topical compositions to small animals such as cats and dogs. Typical of the compositions which may be applied in accord with the principles of my invention are pesticides such as flea killers, shampoos, and deodorizers.

At the present time, topical compositions such as those discussed above are typically applied to small animals in the form of mists, sprays, drenches, and the like.

These current methods of applying topical compositions to small animals have the disadvantage that, in many cases, the application of the composition produces an adverse reaction in the animal being treated because of the hissing sound of a spray, the fumes given off by the composition, etc. This is not only upsetting to the pet being treated but can, also, result in the handler being scratched or bitten.

I have now invented, and disclosed herein, a novel, improved technique for topically applying pharmaceutical and other compositions to animals such as those identified above.

In general, my novel technique for accomplishing the foregoing objective involves the use of a disposable coat which has an animal contactable layer impregnated with the chemical to be applied. This coat is fitted to the animal being treated like any other jacket. Thereafter, gentle massaging motions are employed to "squeeze" the active principle on to the hide of animal being treated. Instead of disturbing the animal, this gentle treatement may actually sooth it. Furthermore, the physical manipulation of the coat by the handler can, in many cases, advantageously be employed to work the active principle past the hairs of the animal into intimate contact with its skin.

After the composition has been transferred to the animal, the coat is removed and discarded in the same fashion as a disposable diaper.

From the foregoing, it will be apparent to the reader that the primary object of my invention resides in the provision of novel, improved methods for applying an essentially unlimited variety of chemical compositions in topical form to small animals.

Other equally important, but more limited, objects of my invention reside in the provision of methods in accord with the preceding object:

which are not upsetting to the animal being treated but may, even, exert a soothing effect on the animal at the same time that the active principle is transferred to it;

which minimize the possibility that the handler of the animal will be scratched, bitten, or otherwise injured in topically applying the active principle to the animal being treated; and which can be carried out rapidly and at relatively low cost.

Still another important object of my invention resides in the provision of certain unique coats which can put on the animal to be treated and thereafter gently manipulated to transfer the active principle from the coat to the skin of the animal.

Related, more specific, but nonetheless important objects of my invention reside in the provision of coats as aforesaid:

which are easy to use; and which can be produced at a low enough cost that they can be disposed of after a single use.

Other important objects and features and additional advantages of my invention will be apparent from the foregoing, the appended claims, and the ensuing detailed description and discussion taken in conjunction with the accompanying drawing in which;

Figure 1:
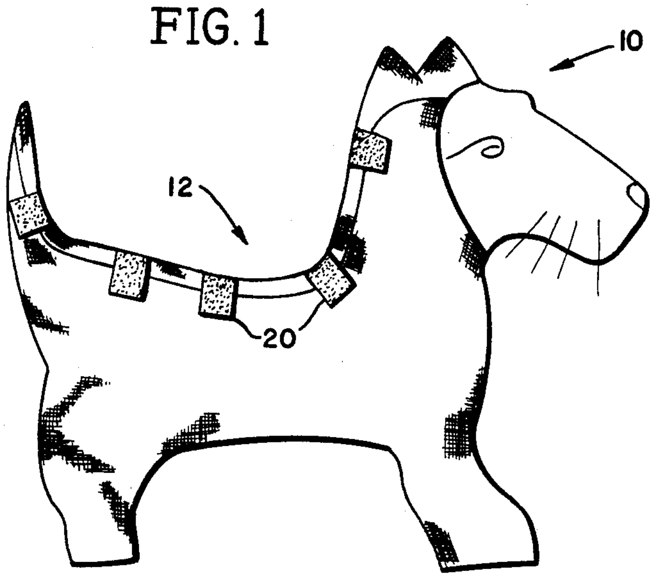
FIG. 1 is a pictorial view of a small animal blanketed with a chemically impregnated coat that can be manipulated in accord with the principles of the present invention to transfer a chemical composition from the coat to the skin of the animal.

Referring now to the drawing, FIG. 1 depicts a small dog 10 jacketed with a coat 12 from which a shampoo, insecticide, skin conditioner, deodorizer, or other chemical can be transferred to the skin of the animal in accord with the principles of my invention.

Figure 3:
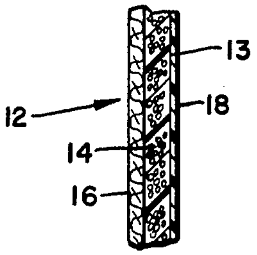
FIG. 3 is a section through the coat taken substantially along line 3—3 of FIG. 2.

Coat 12, which can be readily supplied in different sizes to fit the particular animal being treated, is of the three-layer construction shown in FIG. 3. The coat is configured to expose the face, genital and anal areas of the animal and the bottoms of its feet. Otherwise, it is preferably designed to completely cover the animal.

The central, or core, layer 14 of coat 12 is a flexible, porous or spongelike, material capable of being impregnated with and holding the chemical with which the animal is to be treated. There are a wide variety of commercially available, open cell, polyurethane and other foams which can be employed for this purpose. Among these are the flexible polymers disclosed on pages 507–509, Modern Plastics Encyclopedia, 1983–84, which is hereby incorporated in this disclosure by reference.

Applied to the outer side of core layer 14 is an impervious film 16. This component of coat 12 is used as a liquid and vapor barrier to keep the chemical with which core layer 14 is impregnated from escaping from coat 12.

Outer layer or film 12 can be bonded to core 14 by an appropriate glue, by heat sealing, by ultrasonic bonding, or by any other appropriate technique.

A second, removable, liquid and vapor barrier 18 is applied to the opposite, inner side of core 14 by a conventional releasable adhesive, many of which are available from H. B. Fuller Company, and other commercial sources. Barrier 18 may be fabricated from the same material as outer barrier 16 or from a different one. Again, the particular synthetic from which the inner barrier is fabricated is not critical; and any of a wide selection of commercial materials may be used.

Suitable, flexible, impervious films which can be employed for are included among those described on pages 502–506 of that edition of the Modern Plastics Encyclopedia cited above.

Figure 2:
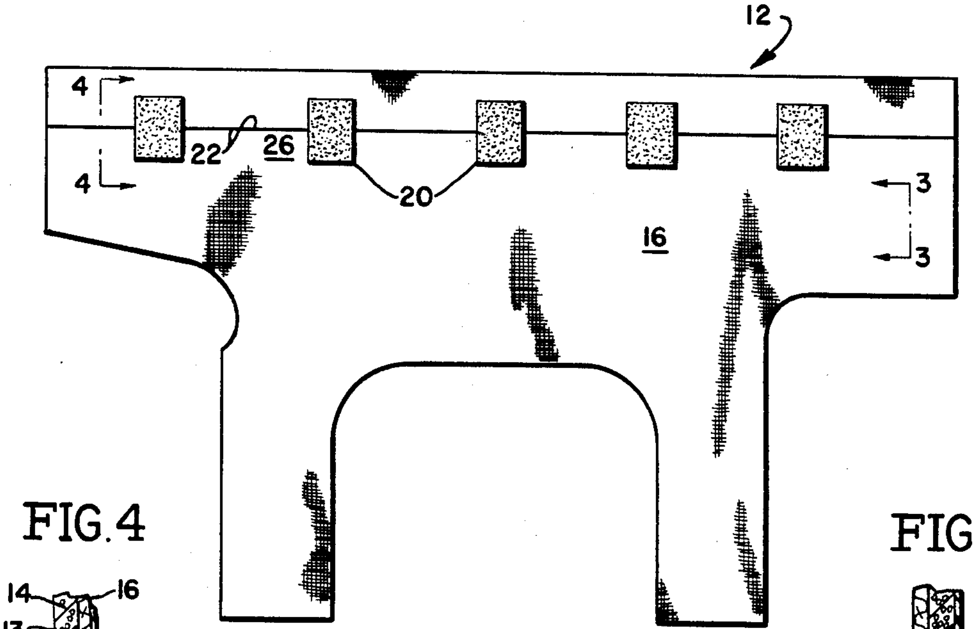
FIG. 2 is a side view of the coat.

Coat 12 is designed to open along a line extending generally along the animal's neck and back but offset to one side as shown in FIG. 2. After the animal is enveloped in coat 12, this opening is closed by fasteners 20.

Figure 4:
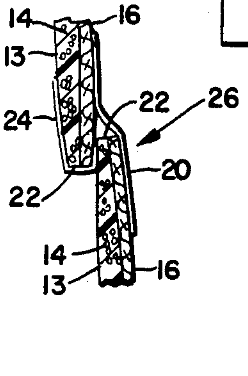
FIG. 4 is a section through the coat taken essentially along line 4—4 of FIG. 1.

As shown in FIG. 4, each of these fasteners includes a backing 24 bonded to the inner side of the coat's core 13 adjacent one of the two edges 22 of the coat. After the animal 10 being treated has been enveloped in the coat, the fasteners 20 are fastened to the second part 26 of the coat to seal the preexisting opening between the two edges of the coat. For this purpose, that part of each fastener's backing member which is engagable with the second, upper edge portion 26 of the coat is coated with a conventional contact adhesive. Again, the particular adhesive that is selected is not critical. A number of useful adhesives are also available from H. B. Fuller Company and other sources.

To use coat 12 to apply a topical composition to the skin of animal 10, the inner protective layer 18 is stripped from core 14. The animal being treated is then enveloped in the coat with the chemically inpregnated core layer 14 next to the animal's skin. Next, fasteners 20 are closed as shown in FIG. 2 to minimize the escape of the active ingredient from the core 14 of coat 12 into the surrounding environment.

Thereafter, coat 12 is gently massaged against the animal's body to transfer the active principle from core 14 of the coat to the animal's skin. After completion of this exercise, tabs 20 are opened, coat 12 removed from animal 10, and disposed of.

As suggested above, this novel technique for transferring wanted compositions to the skin of a subject animal can be accomplished efficiently and without upsetting the animal. Furthermore, coats such as those I have described above can be manufactured at relatively low cost, making it perfectly feasible to dispose of the garment once it has been employed.

As was also discussed above, coat 12 is preferably designed to leave the facial, genital, and anal areas of the animal to which it is applied exposed because of the greater sensitivity in these areas. To ensure overall treatment of the animal, an impregnated, encapsulated sponge (not shown) may be packaged or otherwise supplied with a coat described above. This sponge can be removed from the encapsulating material (a flexible, impervious plastic as described above) and then gently wiped across the exposed areas to complete the treatment.

Again, the material from which the sponge is fabricated, the compositions impregnated in that sponge, and the encapsulating material or materials may be as discussed above in conjunction with the fabrication and use of coat 12.

The invention may also be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A sandwichlike coat or blanketlike device in which a small animal can be enveloped, said device being designed to conform to the body of and encompass the bulk of animal and said device comprising: a flexible, porous inner core layer, the pores of said inner core layer being impregnated with a chemical composition which is to be applied to the skin of the small animal; an essentially impervious outer, flexible layer of uniform thickness bonded to said flexible core to keep said impregnated chemical composition from escaping from said core into the ambient surrounding; an equally impervious film bonded to the inner side of the flexible core to similarly keep said impregnated chemical composition from escaping from said core into the ambient surrounding; and means so bonding said film to the inner side of the flexible core that said film can be stripped from and expose said core and allow said small animal to subsequently be enveloped in said coat with said core contacting said animal to thereby accommodate the transfer of said chemical composition to said animal by the manipulation of said coat.

2. A sandwichlike coat or blanketlike device as designed in claim 1 which is designed to so open that the small animal can be enveloped therein and releasable, adhesively-faced means for thereafter fastening the parts of said device together to affix it to said animal with the core of the device in contact with the animal as aforesaid.

* * * * *